United States Patent [19]
Takebayashi et al.

[11] Patent Number: 5,866,152
[45] Date of Patent: Feb. 2, 1999

[54] SHAMPOO COMPOSITION

[75] Inventors: Yoshihiro Takebayashi; Takao Ishiwatari, both of Toyonaka, Japan

[73] Assignee: Sumitomo Chemical Company, Limited, Osaka, Japan

[21] Appl. No.: 764,255

[22] Filed: Dec. 12, 1996

[30] Foreign Application Priority Data

Dec. 13, 1995 [JP] Japan ..................... 7-324380
Jul. 18, 1996 [JP] Japan ..................... 8-189491

[51] Int. Cl.$^6$ ............... A01N 25/00; A61K 7/075
[52] U.S. Cl. ............. 424/405; 424/70.22; 514/881; 514/919
[58] Field of Search ............... 424/405, 70.22; 514/919, 881

[56] References Cited

U.S. PATENT DOCUMENTS 4,751,225  6/1988  Nishida et al. .
5,256,679  10/1993  Minamida ..................... 514/357
5,612,047  3/1997  Duffy ......................... 424/405

FOREIGN PATENT DOCUMENTS 0908A    6/1989  European Pat. Off. .
0909A1   6/1989  European Pat. Off. .
0 714601 6/1996  European Pat. Off. .

OTHER PUBLICATIONS

Database WPI, Section Ch, Week 9349, 1993, Derwent Publications Ltd., London, GB; Class A97, AN 93–392541.

*Primary Examiner*—Sally Gardner-Lane
*Attorney, Agent, or Firm*—Birch, Stewart, Kolasch & Birch, LLP

[57] ABSTRACT

The present invention provides a shampoo composition effective for control of ectoparasites, particularly for extermination of lice. The shampoo composition may contain 0.001% to 5% by weight of pyriproxyfen, 10% to 70% by weight of an anionic surfactant, 0.5% to 20% by weight of a polyhydric alcohol, and optionally 1% to 8% by weight of a pyrethroid compound.

15 Claims, No Drawings

SHAMPOO COMPOSITION

FIELD OF INVENTION

The present invention relates to a shampoo composition effective for control of ectoparasites, particularly for extermination of lice.

BACKGROUND OF THE INVENTION

In recent years, mass occurrence of lice has been reported from various places of the country, which causes public discussion and calls for establishment of an effective method for extermination of lice.

For extermination of lice, insecticidal dust formulations or shampoos have been used so far. It cannot, however, be said that satisfactory extermination is achieved in every case. There has been a demand for development of a more effective method for extermination of lice.

SUMMARY OF THE INVENTION

The present invention provides a shampoo composition effective for control of ectoparasites, particularly for extermination of lice such as *Pediculus humanus corporis*, *Pediculus humanus humanus* and *Phthirius pubis*. The shampoo composition is obtained by adding pyiiproxyfen (i.e., 4-phenoxyphenyl 2-(2-pyridyloxy)propyl ether) as an active ingredient to a shampoo composition containing an anionic surfactant and further incorporating a polyhydric alcohol for activity enhancement into the composition. That is, the shampoo composition of the present invention comprises 0.001% to 5% by weight of pyriproxyfen, 10% to 70% by weight of an anionic surfactant, and 0.5% to 20% by weight of a polyhydric alcohol.

DETAILED DESCRIPTION OF THE INVENTION

The shampoo composition of the present invention contains, in addition to pyriproxyfen as an active ingredient, an anionic surfactant and a polyhydric alcohol.

Examples of the anionic surfactant used in the present invention may include sulfates, sulfonates, carboxylates, carboxylic acids, phosphates, amino acid salts, and mixtures thereof.

Examples of the sulfate may include polyoxyethylene alkyl ether sulfates such as sodium polyoxyethylene lauryl ether sulfate, higher alcohol sulfates such as sodium lauryl sulfate and lauryl sulfate triethanolamine, polyoxyethylene alkylaryl ether sulfates, glycerin fatty acid ester sulfates, higher fatty acid alkylolamide sulfates, alkyl sulfates, and polyoxyethylene alkyl sulfates. Examples of the sulfonate may include alkylarylsulfonates such as sodium dodecylbenzenesulfonate, alkyl sulfonates, α-olefin sulfonates, higher fatty acid ester sulfonates, dialkylsulfosuccinates such as sodium dioctylsulfosuccinate, and higher fatty acid amide sulfonates such as sodium N-cocoylmethyltaurine. Examples of the carboxylate may include alkyl ether carboxylates such as sodium polyoxyethylene tridecyl ether acetate, and fatty acid soaps. Examples of the carboxylic acid may include alkyl ether carboxylic acids. Examples of the phosphate may include polyoxyethylene alkyl ether phosphates such as sodium polyoxyethylene lauryl ether phosphate, and alkyl phosphates. Examples of the amino acid salt may include N-acylsarcosinates and N-acylalaninates.

In the present invention, one or more anionic surfactants selected from the group consisting of sulfates, sulfonates and carboxylates are preferably used. Particularly preferred are sulfates (e.g., alkyl sulfates, polyoxyethylene alkyl sulfates with the number of moles in the ethylene oxide units added being 1 to 4).

In the shampoo composition of the present invention, the anionic surfactant or surfactants are contained at 10% to 70% by weight, preferably 10% to 50% by weight, based on the total weight of the composition.

The shampoo composition of the present invention may further comprise other surfactants, if required, e.g., nonionic surfactants such as amine oxide surfactants, polyoxyethylene polyoxypropylene block copolymers, polyoxyethylene sorbitan fatty acid esters and polyoxyethylene alkyl phenyl ethers.

Examples of the polyhydric alcohol used in the present invention may include ethylene glycol, propylene glycol, 1,3-butylene glycol, or homopolymers and copolymers of these glycols, and glycerin. When polyethylene glycol is used as the polyhydric alcohol, the weight average molecular weight of the polyethylene glycol is preferably 300 to 6000. When polypropylene glycol is used, the weight average molecular weight of the polypropylene glycol is preferably 400 to 2000. When polyoxyethylene-polyoxypropylene copolymer is used, the weight average molecular weight of the polyoxy-ethylene-polyoxypropylene copolymer is preferably 3000 to 15,000.

The above polyhydric alcohols may be used alone or in combination. In the shampoo composition of the present invention, the polyhydric alcohol or alcohols are contained at 0.5% to 20% by weight, preferably 2.5% to 12.5% by weight, based on the total weight of the composition.

The shampoo composition of the present invention is usually composed of 0.001% to 5% by weight of pyriproxyfen, 10% to 70% by weight of an anionic surfactant, 0.5% to 20% by weight of a polyhydric alcohol, and water as the balance. The preparation of the shampoo composition may be achieved by mixing these ingredients and heating the resulting mixture under stirring. If required, the shampoo composition of the present invention may further comprises additional insect-controllable agents (e.g., pyrethroid compounds such as phenothrin, permethrin, allethrin, empenthrin, prallethrin, transfluthrin, imiprothrin, tetramethrin, resmethrin and 1-ethynyl-2-fluoro-2-pentenyl 3-(2,2-dichlorovinyl)-2,2-dimethylcyclopropanecarboxylate, insect growth regulators, repellants), preservatives, perfumes, pigments, buffers, pH regulating agents, antioxidants, viscosity regulating agents, foam stabilizing agents, chelating agents and conditioning agents.

When a pyrethroid compound is used as the additional insect-controlling agent, it may usually be contained in the shampoo composition of the present invention at 1% to 8% by weight, based on the total weight of the composition. As the pyrethroid compound, phenothrin, permethrin, allethrin or empenthrin is preferably used.

The shampoo composition of the present invention, although it is effective for extermination of lice, ticks, fleas and bedbugs, which are ectoparasitic on the human body, can also be effective for extermination of fleas, ticks, lice, flies, houseflies, biting midges and biting lice, which are ectoparasitic on pets such as cats, dogs and rabbits, on domestic animals such as cattle, horses, swine, sheep and goats, and on domestic fowls such as ducks, chickens and geese, and the shampoo composition can also be used for these animals.

The shampoo composition of the present invention may be used for treatment of animals or the like by ordinary procedure, for example, by wetting their body hair with water, applying the shampoo composition neat or after diluted with water to a prescribed concentration, followed by uniform treatment with a brush or the like, and, if necessary, rinsing with water. The amount of shampoo composition used, although it may vary with the kind of animal treated and volume of body hair, is preferably such that pyriproxyfen as the active ingredient is applied at a ratio of 0.005 mg/cm$^2$ or higher. When formulated into a concentrate, the shampoo composition of the present invention may preferably be used in the form of a water dilution previously prepared, which is more effective for uniform treatment.

The present invention will be further illustrated by the following Production Examples and Test Examples. Three shampoo compositions containing no polyhydric alcohol for comparison of lice extermination effects are provided as Reference Examples.

PRODUCTION EXAMPLE 1

To 66.7 parts by weight of NIKKOL® SBL-4T (30% aqueous solution of polyoxyethylene (4) lauryl sulfate triethanolamine, available from Nikko Chemicals) were added 0.1 part by weight of pyriproxyfen and 5 parts by weight of polyethylene glycol (weight average molecular weight, 400), followed by addition of distilled water to bring the resulting mixture to 100 parts by weight in total. The mixture was then heated to 70° C. and stirred, which afforded a shampoo composition of the present invention.

PRODUCTION EXAMPLE 2

A shampoo composition of the present invention was obtained in the same manner as described in Production Example 1, except that the amount of polyethylene glycol (weight average molecular weight, 400) added was changed from 5 parts by weight to 10 parts by weight.

PRODUCTION EXAMPLE 3

To 66.7 parts by weight of NIKKOL® TEALS-42 (42% aqueous solution of lauryl sulfate triethanolamine, available from Nikko Chemicals) were added 0.1 part by weight of pyriproxyfen and 5 parts by weight of propylene glycol, followed by addition of distilled water to bring the resulting mixture to 100 parts by weight in total. The mixture was then heated to 70° C. and stirred, which afforded a shampoo composition of the present invention.

PRODUCTION EXAMPLE 4

A shampoo composition of the present invention was obtained in the same manner as described in Production Example 3, except that the amount of propylene glycol added was changed from 5 parts by weight to 10 parts by weight.

PRODUCTION EXAMPLE 5

To 66.7 parts by weight of NIKKOL® TEALS-42 were added 0.1 part by weight of pyriproxyfen and 10 parts by weight of polypropylene glycol (weight average molecular weight, 2000), followed by addition of distilled water to bring the resulting mixture to 100 parts by weight in total. The mixture was then heated to 70° C. and stirred, which afforded a shampoo composition of the present invention.

PRODUCTION EXAMPLE 6

To 20 parts by weight of NIKKOL® ECTD-3NEX (sodium polyoxyethylene (3) tridecyl ether acetate, available from Nikko Chemicals) were added 0.1 part by weight of pyriproxyfen and 10 parts by weight of propylene glycol, followed by addition of distilled water to bring the resulting mixture to 100 parts by weight in total. The mixture was then heated to 70° C. and stirred, which afforded a shampoo composition of the present invention.

PRODUCTION EXAMPLE 7

To 66.7 parts by weight of NIKKOL® SBL-4T were added 0.1 part by weight of pyriproxyfen, 4 parts by weight of d-phenothrin and 10 parts by weight of propylene glycol, followed by addition of distilled water to bring the resulting mixture to 100 parts by weight in total. The mixture was then heated to 70° C. and stirred, which afforded a shampoo composition of the present invention.

PRODUCTION EXAMPLE 8

To 66.7 parts by weight of NIKKOL® SBL-4T were added 0.1 part by weight of pyriproxyfen, 4 parts by weight of permethrin and 10 parts by weight of propylene glycol, followed by addition of distilled water to bring the resulting mixture to 100 parts by weight in total. The mixture was then heated to 70° C. and stirred, which afforded a shampoo composition of the present invention.

PRODUCTION EXAMPLE 9

To 66.7 parts by weight of NIKKOL® SBL-4T were added 0.5 part by weight of pyriproxyfen and 5 parts by weight of polyethylene glycol (weight average molecular weight, 400), followed by addition of distilled water to bring the resulting mixture to 100 parts by weight in total. The mixture was then heated to 70° C. and stirred, which afforded a shampoo composition of the present invention.

REFERENCE EXAMPLE 1

To 66.7 parts by weight of NIKKOL® SBL-42T was added 0.1 part by weight of pyriproxyfen, followed by addition of distilled water to bring the resulting mixture to 100 parts by weight in total. The mixture was then heated to 70° C. and stirred, which afforded a shampoo composition for comparison.

REFERENCE EXAMPLE 2

To 66.7 parts by weight of NIKKOL®TEALS-42 was added 0.1 part by weight of pyriproxyfen, followed by addition of distilled water to bring the resulting mixture to 100 parts by weight in total. The mixture was then heated to 70° C. and stirred, which afforded a shampoo composition for comparison.

REFERENCE EXAMPLE 3

To 20 parts by weight of NIKKOL® ECTD-3NEX was added 0.1 part by weight of pyriproxyfen, followed by addition of distilled water to bring the resulting mixture to 100 parts by weight in total. The mixture was then heated to 70° C. and stirred, which afforded a shampoo composition for comparison.

TEST EXAMPLE 1

The shampoo compositions obtained in Production Examples 1 to 6 and Reference Examples 1 to 3 were independently diluted with distilled water to the respective prescribed concentrations (dilution ratios are shown in Table 1), and then put into separate polyethylene cups. A small piece of nylon gauze with a size of 2 cm×2 cm, on which about 20 eggs of Pediculus humanus corporis had been laid on that or previous day, was dipped into the solution in one of the polyethylene cups for 5 seconds. These small pieces of nylon gauze were washed with warm water for 1 minute, and then placed in an incubator at 30° C. After 10 days, the degree of hatching inhibition against lice was examined.

The results are shown in Table 1.

TABLE 1

| Test composition obtained in | Dilution ratio (by volume) | Degree of hatching inhibition (%) |
|---|---|---|
| Production Example 1 | 100-fold | 95.9 |
| Production Example 2 | 100-fold | 100 |
| Production Example 3 | 200-fold | 100 |
| Production Example 4 | 200-fold | 100 |
| Production Example 5 | 200-fold | 100 |
| Production Example 6 | 200-fold | 100 |
| Reference Example 1 | 100-fold | 75.0 |
| Reference Example 2 | 200-fold | 51.4 |
| Reference Example 3 | 200-fold | 75.5 |

TEST EXAMPLE 2

The shampoo compositions obtained in Production Examples 7 and 8 were independently diluted with distilled water by a factor of 30, and then put into separate polyethylene cups. A small piece of nylon gauze with a size of 2 cm×2 cm, on which about 20 eggs of Pediculus humanus corporis had been laid on that or previous day was packed, together with 20 adults of Pediculus humanus corporis about 5 days old after emergence, in a ball-shaped tea strainer of stainless steel (diameter, 5 cm), which was then dipped into the solution in one of the polyethylene cups for 5 seconds. These ball-shaped tea strainers were washed with warm water for 1 minutes, and then placed in an incubator at 30° C. The adults and hatched larvae were provided with blood suck as the feed once a day. After 10 days, the number of surviving lice (including larvae hatched from the eggs) was examined.

The results are shown in Table 2. The survival rates reported in Table 2 were calculated by the following equation.

TABLE 2

$$\text{Survival rate (\%)} = \frac{\text{Number of surviving adults} + \text{Number of surviving larvae}}{40} \times 100$$

| Test composition obtained in | Survival rate (%) |
|---|---|
| Production Example 7 | 0 |
| Production Example 8 | 0 |
| No treatment | 82.5 |

TEST EXAMPLE 3

The shampoo composition obtained in Production Example 9 was taken at a weight of 10 g in a 20 ml vial, in which 0.5 g of cut wool hairs was dipped. After 30 minutes, the treated wool hairs were removed and rinsed with 50 ml of distilled water, followed by three repetitions of removing and rinsing with fresh distilled water. The rinsed wool hairs were air-dried overnight and used for the following efficacy test.

In a 50 ml glass vessel were placed 0.5 g of the air-dried wool hairs and then 60 eggs of cat fleas, followed by allowing to stand undisturbed for 2 hours. The eggs were then transferred to a Petri dish and maintained at 26° C. under 90% humidity. After 4 days, the degree of hatching inhibition against cat fleas was examined, and it was found that the shampoo composition exhibited satisfactory hatching inhibition.

What is claimed is:

1. A shampoo composition comprising 0.001% to 5% by weight of pyriproxyfen, 10% to 70% by weight of an anionic surfactant selected from the group consisting of alkyl ether carboxylates and sulfates, and 0.5% to 20% by weight of a polyhydric alcohol which is propylene glycol or polypropylene glycol of molecular weight 400–2000.

2. A shampoo composition according to claim 1, further comprising 1% to 8% by weight of a pyrethroid compound.

3. A shampoo composition according to claim 2, wherein the pyrethroid compound is at least one selected from the group consisting of phenothrin, permethrin, allethrin and empenthrin.

4. A shampoo composition according to claim 1 or 2, wherein the anionic surfactant is at least one polyoxyethylene alkyl sulfate.

5. A shampoo composition according to claim 1 or 2, which is used for extermination of lice.

6. A method for controlling ectoparasites, comprising applying a shampoo composition according to claim 1 or 2 to humans, pets, domestic animals or domestic fowls.

7. The shampoo composition according to claim 4, wherein said polyoxyethylene alkyl sulfate is polyoxyethylene lauryl sulfate.

8. The shampoo composition according to claim 1, comprising 10% to 50% by weight of the anionic surfactant.

9. The shampoo composition according to claim 1 or claim 8, comprising 2.5% to 12.5% by weight of the polyhydric alcohol 3.

10. The method according to claim 6, wherein an amount of said pyriproxyfene in said shampoo composition, as applied is 0.005 mg/cm$^2$ or higher.

11. A method for controlling ectoparasites, comprising shampooing humans, pets, domestic animals or domestic fowls with an effective ectoparasite controlling amount of the shampoo composition according to claim 1 or 2.

12. The shampoo composition according to claim 1 or 2, wherein the anionic surfactant is selected from alkyl ether carboxylates.

13. The shampoo composition according to claim 1 or 2, wherein the anionic surfactant is selected from sulfates.

14. The shampoo composition according to claim 1 or 2, wherein the polyhydric alcohol is propylene glycol.

15. The shampoo composition according to claim 1 or 2, wherein the polyhydric alcohol is polypropylene glycol of molecular weight 400–2000.

* * * * *